United States Patent
George et al.

(10) Patent No.: US 10,953,144 B2
(45) Date of Patent: Mar. 23, 2021

(54) LIP-ENHANCEMENT DEVICE AND METHOD

(71) Applicant: L'OREAL, Paris (FR)

(72) Inventors: Kelly George, Denville, NJ (US); Zane Miller, Seattle, WA (US); Janet Wangari-Talbot, Hillsborough, NJ (US); Destenee Green, Jersey City, NJ (US)

(73) Assignee: L'OREAL, Paris (FR)

( * ) Notice: Subject to any disclaimer, the term of this patent is extended or adjusted under 35 U.S.C. 154(b) by 329 days.

(21) Appl. No.: 15/639,978

(22) Filed: Jun. 30, 2017

(65) Prior Publication Data
US 2019/0001033 A1  Jan. 3, 2019

(51) Int. Cl.
*A61M 1/08* (2006.01)
*A61H 9/00* (2006.01)
*A61M 39/22* (2006.01)

(52) U.S. Cl.
CPC ............ *A61M 1/08* (2013.01); *A61H 9/0007* (2013.01); *A61H 9/0057* (2013.01);
(Continued)

(58) Field of Classification Search
CPC ........ A61M 1/08; A61M 1/00; A61M 1/0066; A61M 1/0068; A61M 2230/005; A61M 2205/07; A61M 2210/0637; A61M 2210/0625; A61M 2209/06; A61H 9/0007; A61H 9/0057; A61H 2201/0153; A61H 2201/0176; A61H 2201/018; A61H 2201/105; A61H 2201/169; A61H 2201/5005; A61H 2201/0107; A61H 2201/0157; A61H 2201/0196; A61H 2201/1645; A61H 2201/1604; A61H 2205/02; A61H 2205/022; A61H 2205/026; A61H 7/00; A61H 7/001; A61H 7/007; A61H 7/008; A45D 33/26; A45D 33/28; A45D 40/00; A45D 40/18; A45D 40/24; A45D 2040/0018; A45D 2040/0043;
(Continued)

(56) References Cited

U.S. PATENT DOCUMENTS

| 15,626 | A | * | 8/1856 | Tillotson | ................ | A61H 9/005 601/6 |
| 67,663 | A | * | 8/1867 | Mattson | ................ | A61H 9/005 601/6 |

(Continued)

OTHER PUBLICATIONS

Partial International Search dated Sep. 25, 2018 in PCT/US2018/039741, citing documents AA and AB therein, 15 pages.
(Continued)

*Primary Examiner* — Rachel T Sippel
*Assistant Examiner* — Benjamin M. Kusiak
(74) *Attorney, Agent, or Firm* — Oblon, McClelland, Maier & Neustadt, L.L.P.

(57) ABSTRACT

An apparatus is provided for lip conditioning, including a mouthpiece having an opening configured to press against a portion of tissue or lips of a user; and a chamber configured to receive the portion of the tissue or lips of the user through the opening, wherein the apparatus is configured to generate suction within the chamber, and to apply a negative pressure to a portion of tissue or lips of a user.

18 Claims, 8 Drawing Sheets

(52) U.S. Cl.
CPC ....... *A61M 39/22* (2013.01); *A61H 2201/018* (2013.01); *A61H 2201/0153* (2013.01); *A61H 2201/0176* (2013.01); *A61H 2201/105* (2013.01); *A61H 2201/169* (2013.01); *A61H 2201/5005* (2013.01); *A61H 2205/02* (2013.01); *A61H 2205/022* (2013.01); *A61M 2209/06* (2013.01); *A61M 2210/0625* (2013.01)

(58) Field of Classification Search
CPC ...... A45D 2040/005; A45D 2040/0056; A45D 2040/0025
USPC ............ 601/1, 6, 7, 8, 10–12; 132/294, 297, 132/317, 318, 320
See application file for complete search history.

(56) References Cited

U.S. PATENT DOCUMENTS

| | | | | |
|---|---|---|---|---|
| 961,365 | A * | 6/1910 | McCall | A61H 9/005 601/7 |
| 1,460,927 | A * | 7/1923 | Thompson | A61H 7/00 601/6 |
| 2,052,098 | A * | 8/1936 | Lockett | A61H 9/005 601/10 |
| 2,189,116 | A * | 2/1940 | Niemiec | A61H 9/005 601/6 |
| 2,238,541 | A * | 4/1941 | Spagnolo | A61H 9/0021 15/397 |
| 3,841,322 | A * | 10/1974 | Spelio | A61H 9/005 601/9 |
| 4,836,192 | A * | 6/1989 | Abbate | A61H 9/005 601/7 |
| 5,902,293 | A * | 5/1999 | Liu | A61H 9/005 601/14 |
| 7,144,390 | B1 * | 12/2006 | Hannigan | A61F 7/10 604/313 |
| 7,287,923 | B1 * | 10/2007 | Chen | A45D 40/24 132/317 |
| 2003/0062060 | A1 * | 4/2003 | Burroughs | A45C 11/008 132/297 |
| 2004/0106907 | A1 * | 6/2004 | Liu | A61H 9/005 604/313 |
| 2004/0236254 | A1 * | 11/2004 | Nichols | A61H 7/005 601/6 |
| 2005/0172446 | A1 * | 8/2005 | Fujisato | A47K 7/04 15/322 |
| 2006/0116612 | A1 * | 6/2006 | Drysdale | A61H 9/005 601/10 |
| 2007/0225621 | A1 * | 9/2007 | Sebastian | A61H 7/00 601/6 |
| 2007/0265586 | A1 * | 11/2007 | Joshi | A61M 1/0031 604/313 |
| 2009/0118573 | A1 * | 5/2009 | Tsao | A61M 1/06 600/38 |
| 2010/0137256 | A1 | 6/2010 | Haddad | |
| 2011/0020047 | A1 * | 1/2011 | Kim | A45D 34/045 401/35 |
| 2013/0046211 | A1 * | 2/2013 | Ho | A61M 1/08 601/6 |
| 2013/0110014 | A1 * | 5/2013 | Luzon | A61H 9/0057 601/6 |
| 2014/0081183 | A1 * | 3/2014 | Gomez | A61H 9/0057 601/6 |
| 2014/0135175 | A1 | 5/2014 | Shepherd et al. | |
| 2016/0045389 | A1 * | 2/2016 | Goonetilleke | A61H 9/0057 601/11 |
| 2016/0242989 | A1 * | 8/2016 | Alexander | A61H 9/0057 |
| 2016/0349128 | A1 * | 12/2016 | Kaufmann | G01L 7/084 |
| 2018/0042360 | A1 * | 2/2018 | Gibson | A45D 33/006 |
| 2018/0164173 | A1 * | 6/2018 | Gammon | G01L 7/163 |
| 2018/0344012 | A1 * | 12/2018 | Yarbrough | A45D 40/265 |

OTHER PUBLICATIONS

International Search Report and Written Opinion dated Nov. 16, 2018 in PCT/US2018/039741.

* cited by examiner

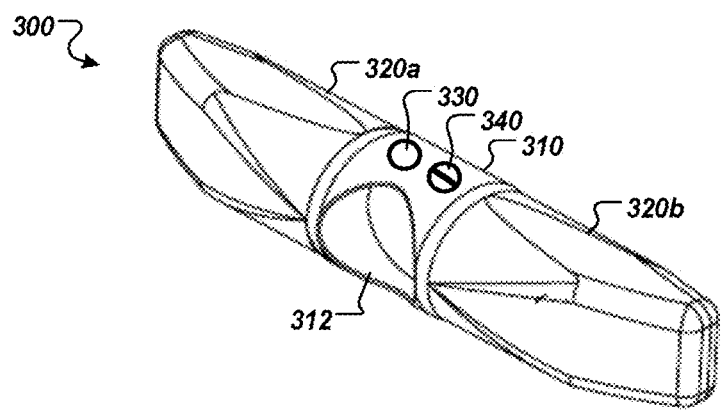
FIG. 3A
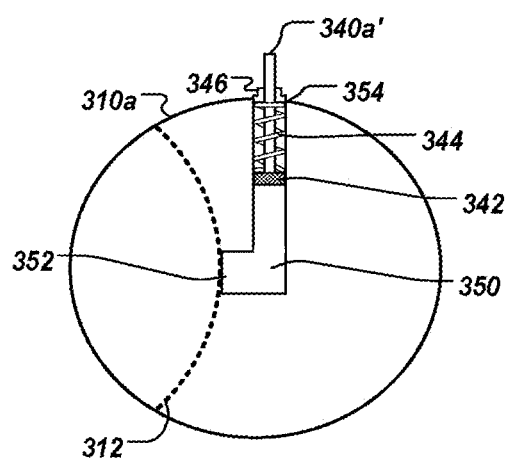
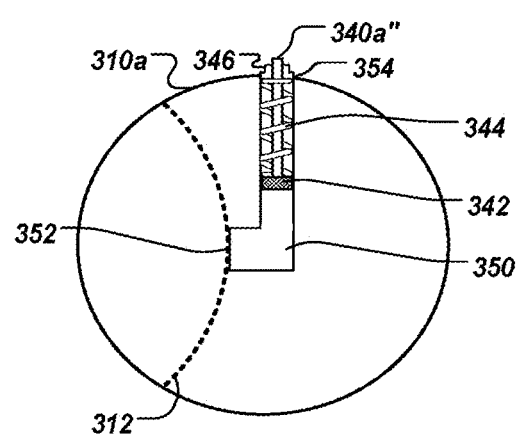
FIG. 3B          FIG. 3C

LIP-ENHANCEMENT DEVICE AND METHOD

BACKGROUND

The present disclosure describes a personal care tool for use in beauty, care, and conditioning of lip tissue.

SUMMARY

According to an embodiment, an apparatus is provided for lip conditioning, comprising: a mouthpiece having an opening configured to press against a portion of tissue or lips of a user; and a chamber configured to receive the portion of the tissue or lips of the user through the opening, wherein the apparatus is configured to generate suction within the chamber, and to apply a negative pressure to a portion of tissue or lips of a user.

According to an embodiment, the negative pressure is configured to allow the blood vessels within the tissue or lips of the user to fill with blood and to trigger an inflammatory response of chemicals.

According to an embodiment, the opening of the mouthpiece has a contoured edge configured to press against the portion of tissue or lips of the user.

According to an embodiment, the apparatus further comprises an access port disposed at a surface inside the chamber which connects to a pressure valve.

According to an embodiment, the access port includes a sensor that connects to an indicator on an exterior surface of the apparatus for indicating that a pressure change has occurred in the chamber.

According to an embodiment, the apparatus further comprising at least one compartment configured to hold one or more accessories.

According to an embodiment, the one or more accessories include at least one of a topical applicator, a lipstick tube, and an exfoliator.

According to an embodiment, there are at least two compartments disposed on opposite sides of the chamber, and each of at least two of the topical applicator, lipstick tube, and exfoliator are separately disposed in the two compartments respectively.

According to an embodiment, the at least one compartment includes a removable cap, an inner surface of which forms a portion of the at least one compartment.

According to an embodiment, the at least one compartment is configured to hold at least two of the accessories, where one of the two accessories is configured to attach to a surface of the removable cap.

According to an embodiment, the at least one compartment includes an applicator interface configured to connect with any one of the one or more accessories such that the one or more accessories are interchangeable.

According to an embodiment, the apparatus further comprises a gauge indicator connected to the chamber that includes a spring a piston which is configured to move based on a change in an amount of suction pressure in the chamber.

According to an embodiment, the apparatus further comprises a pneumatic vibrator configured to generate a vibration at a predetermined frequency.

According to an embodiment, the pneumatic vibrator is configured to generate a cyclic negative pressure at the predetermined frequency.

According to an embodiment, the apparatus further includes a screen disposed covering the opening.

According to an embodiment, the screen includes openings configured to allow protrusions of the lip tissue through one or more portions screen.

According to an embodiment, the apparatus is configured to apply a cyclic negative pressure to a portion of tissue or lips.

According to an embodiment, the apparatus is configured to apply a cyclic negative pressure to a portion of tissue or lips of a frequency and for a duration sufficient to elicit blood within the tissue or lips.

According to an embodiment, the apparatus is configured to apply a cyclic negative pressure to a portion of tissue or lips of a frequency to elicit blood within the tissue or lips.

According to an embodiment, the apparatus is configured to apply a cyclic negative pressure to a portion of tissue or lips of an amplitude and for a duration sufficient to elicit blood within the tissue or lips without bruising of the tissue or lips.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 3A is a perspective drawing of a lip device including a mouthpiece further including a gauge indicator and a pneumatic vibrator according to an example;

FIGS. 3B-3C are drawings of a cross section of a mouthpiece including a gauge indicator having a calibrated spring and piston according to an example;

DETAILED DESCRIPTION

A lip device is provided for performing lip therapy and conditioning a portion of lip tissue of a user. The lip device can be used by the user to enhance their lip volume, give an appearance of plumper lips, and to modify a lip color. Use of the lip device is configured to improve an overall condition of the lip tissue including increased moisture retention resulting in soft and smooth lips, as well as visible reduction in aging of the lips such as reduction of fine lines/wrinkles around the lip.

Figure 7:
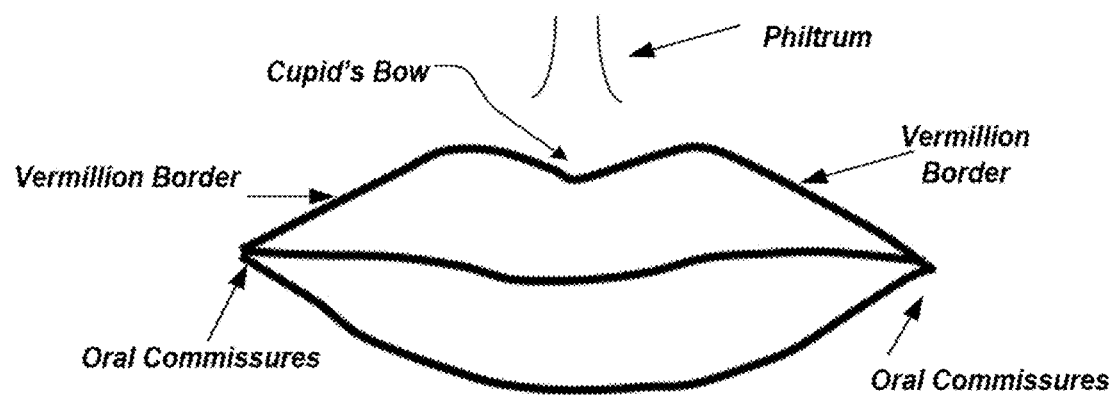
FIG. 7 shows the anatomy of a user's lip region.

FIG. 7 shows the perioral region of a user, and corresponding features (such as the "Cupid's Bow", Philtrum, Vermillion Border, Oral Commissures) which comprises the lower one third of the face, which consists of the upper and lower lips, the nasolabial folds, and the chin.

Lip tissue is composed of layers including the epidermis, subcutaneous tissue, orbicularis oris muscle fibers, and mucosa, from superficial to deep respectively. Within a top lip and a bottom lip respectively, a superior labial artery and an inferior labial artery course between the orbicularis muscle fibers and the mucosa. The lip tissue includes the vermilion that is composed of non-keratinized squamous epithelium that covers numerous capillaries. The capillaries give the vermilion its characteristic color. Lip tissue further includes numerous minor salivary glands. In an aspect, the lip device can be configured to trigger fiberblast cells within the lip tissue to express proteins, self-proliferate, and generate collagen production.

Referring now to the drawings, wherein like reference numerals designate identical or corresponding parts throughout the several views.

Figure 1A:
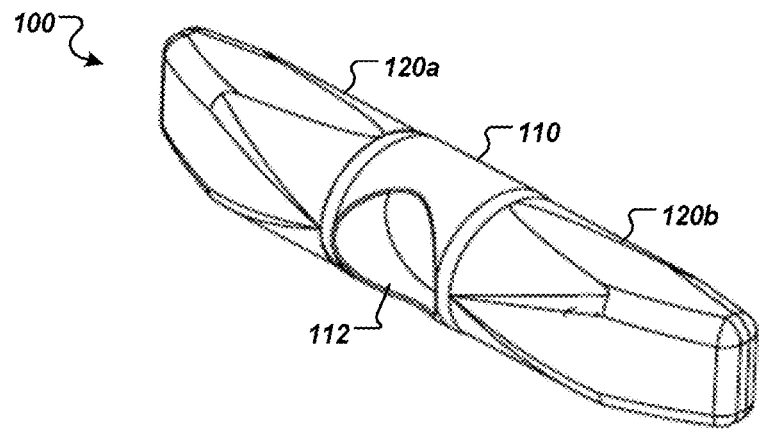
FIG. 1A is a perspective drawing of a lip device including a mouthpiece having a chamber configured to press against portion of tissue or lips of a user, and a pair of end caps according to an example.

FIG. 1A is a perspective drawing of a lip device 100 including a mouthpiece 110 having a chamber 112 configured to press against portion of tissue or lips of a user, and a pair of end caps 120a-b according to an example.

Figure 1B:
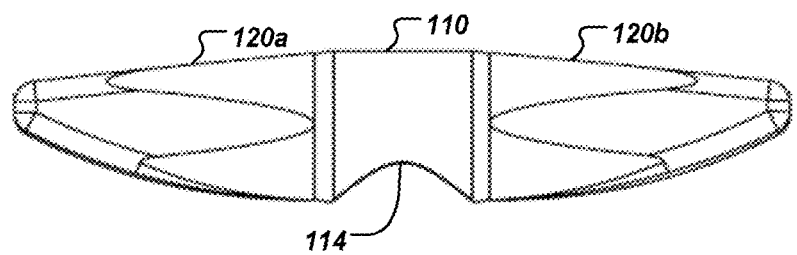
FIG. 1B is a drawing from a top of the lip device showing the mouthpiece having a cupping curvature configured to press against a portion of the lips of the user according to an example.

FIG. 1B is a drawing from a top of the lip device 100 showing the mouthpiece 110 having a cupping curvature or contour 114 configured to press against a portion of the lips of the user according to an example.

Figure 1C:
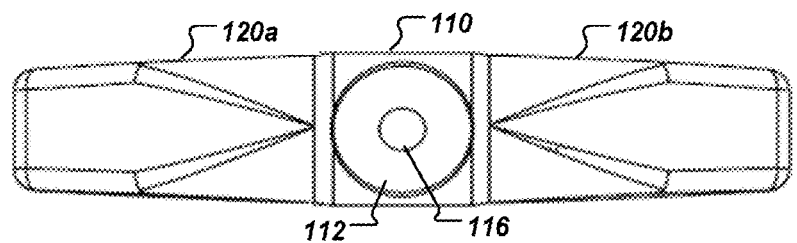
FIG. 1C is a drawing from a front of the lip device viewing into the mouthpiece according to an example.

FIG. 1C is a drawing from a front of the lip device 100 viewing into the mouthpiece 110 according to an example. In an example, the mouthpiece 110 can have a sensor and/or an access port 116. The access port 116 may provide a connecting conduit to activate a pressure valve (not shown), and it may be equipped with a sensor that connects to an indicator knot shown) when there is a detected pressure change in the chamber.

In an aspect, during operation, a user places a portion of the lips within the chamber 112 of the mouthpiece 110 where at least a portion of the lips is subjected to and applied vacuum or suction generated by the lip device 100. In an aspect, during operation, a negative pressure is formed that is configured to allow the blood vessels within the lip tissue to fill with blood and to trigger an inflammatory response of chemicals such as histamines and leukotrienes. Filling the lip tissue with blood performs a dual function of increasing the lip volume and creating a more rosy lip color. The negative pressure may be aided or triggered by suction provided by the user.

FIGS. 2A-2B

In an example, the lip device can include one or more accessories such as a topical applicator, a lipstick tube, and an exfoliator. In an example, the lip device can have a built-in accessory. In an example, the lip device can have replaceable or exchangeable accessories.

Figure 2A:
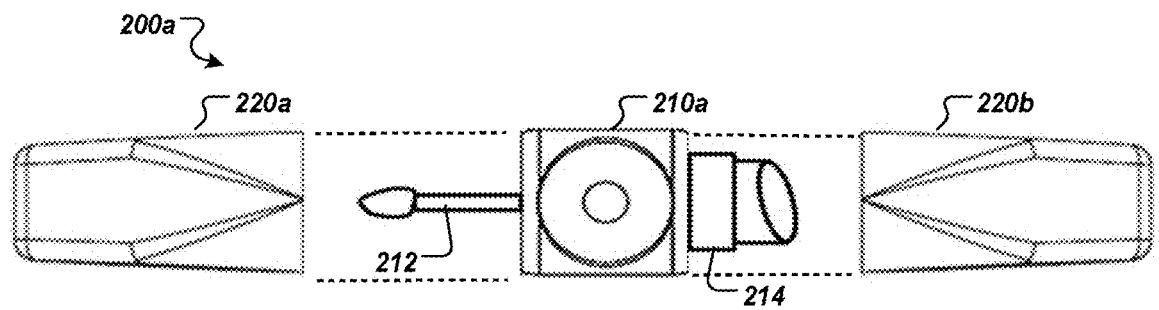
FIG. 2A is a drawing of an expanded view of a lip device including a mouthpiece having a topical applicator, a lipstick tube, and the pair of end caps removed from the mouthpiece according to an example.
Figure 2B:
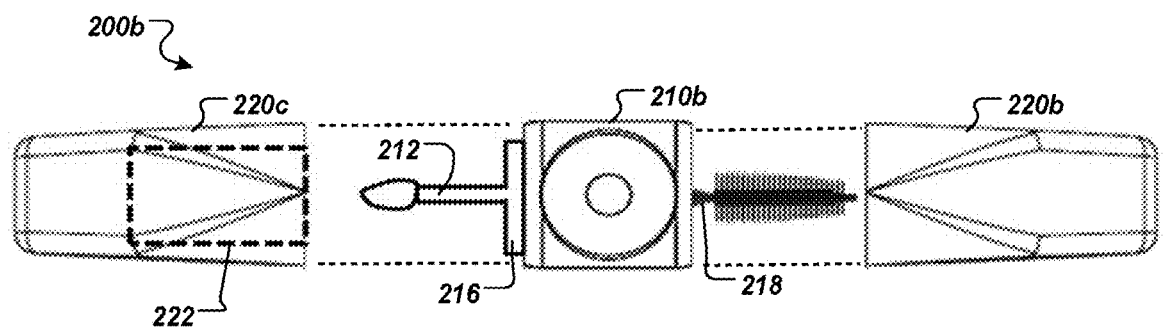
FIG. 2B is a drawing of an expanded view of a lip device including a mouthpiece having an applicator plug, an exfoliating brush, and an end cap having a topical reservoir according to an example.

FIGS. 2A and 2B show pictures of expanded views of a lip device 200a-b including a mouthpiece 210a-b further having accessory attachments 212-218. As shown in FIG. 2A, the mouthpiece 210a further includes a topical applicator 212 and a lipstick tube 214 attached to opposing ends of the mouthpiece 210a according to an example. The pair of end caps 220a-b are removed from the mouthpiece 210a. As shown in FIG. 2B, the mouthpiece 210b further includes an applicator plug 216 having the topical applicator 212 and an exfoliating brush 218 attached to opposing ends of the mouthpiece 210b according to an example. The lip device 200b further includes an end cap 220c, having a topical reservoir 222 configured to be secured by the applicator plug 216, and an endcap 220b configured to cover the exfoliating brush 218 according to an example. Use of the exfoliating brush 218 is configured to aid in removal of dead skin cells, which speeds up renewal process of the lip tissue.

In an example, the lipstick tube 214 can hold lip balm/ active configured to hydrate the lip tissue. In an aspect, chemicals in some lipsticks can dry lip tissue and putting on the lip balm/active will cancel that effect.

The topical applicator 212 can be used to deliver a lip serum to the user's lip. In an example, the lip serum can contain a variety of actives for modifying a lip tissue, supporting the lip tissue, and for modifying a color of the lip tissue. Examples of actives for modifying the lip tissue include hyaluronic acid microspheres configured to retain moisture in the lip tissue. Examples of actives for supporting the lip tissue include collagen configured to fill in lip lines. Examples of actives for modifying a color of the lip tissue include cinnamon, capsacin, and wintergreen to restore a natural rosy look to the lips.

FIGS. 3A-3E

In an aspect, the lip device 100 can be configured to create a cyclic negative pressure to enhance the tissue therapy. In an aspect, the lip device 100 can be configured to apply a cyclic negative pressure to a biological surface. In an aspect, the lip device 100 can be configured to apply the tissue therapy including delivering of a cyclic negative pressure stimulus to a biological surface. In an embodiment, the lip device 100 is configured to apply a cyclic negative pressure to a portion of tissue or lips. In an embodiment, the lip device 100 is configured to apply a cyclic negative pressure to a portion of tissue or lips of a frequency and for a duration sufficient to elicit blood within the tissue or lips. In an embodiment, the lip device 100 is configured to apply a cyclic negative pressure to a portion of tissue or lips of a frequency to elicit blood within the tissue or lips. In an embodiment, the lip device 100 is configured to apply a cyclic negative pressure to a portion of tissue or lips of an amplitude and for a duration sufficient to elicit blood within the tissue or lips without bruising of the tissue or lips.

In an example, the cyclic negative pressure is configured to generate a vibration at a therapeutic frequency. In an example, the cyclic negative pressure is a change between two or more negative pressures at a therapeutic frequency. In an aspect, the therapeutic frequency is configured to prevent bruising of the lip tissue. For example, in an embodiment, the therapeutic frequency is of an amplitude and for a duration sufficient to prevent bruising of the lip tissue. FIG. 3A is a perspective drawing of a lip device 300 including a mouthpiece 310 having a chamber 312, a pneumatic vibrator 330, and a gauge indicator 340 according to an example.

FIGS. 3B-3C are drawings of a cross section of a mouthpiece 310a having a channel 350 with a first end 352 with access to the chamber 312 and a second end 354, which includes a protruding portion 346, connected to a gauge indicator 340a-b according to an example. In an example, the gauge indicator 340a' or 340a" can have a spring 344 and a piston 342 that can be calibrated to move based on an absolute and/or change in an amount of suction pressure with a predetermined setting. In another example, the gauge indicator 340a can be configured to be calibrated by the user.

In an example, the gauge indicator 340a can be moved by a negative pressure due to suction pressure from a first position 340a' to a second position 340a".

Figure 3D:
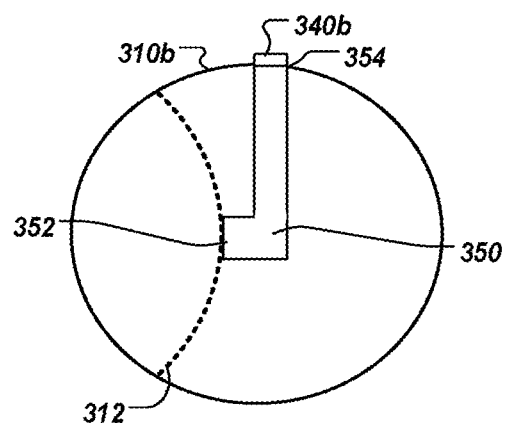
FIG. 3D is a drawing of a cross section of a mouthpiece having a gauge indicator having a pressure sensor and digital indicator according to an example.

FIG. 3D is a drawing of a cross section of a mouthpiece 310b having a channel 350 with a first end 352 with access to the chamber 312 and a second end 354 connected to a gauge indicator 340b having a pressure sensor and digital indicator according to an example. In an example, the pressure sensor configured to detect an absolute and/or change in an amount of suction pressure. In an example, the pressure sensor can be configured to detect a negative pressure. In an example, the pressure sensor can be configured to detect a length of time at a negative pressure.

Figure 3E:
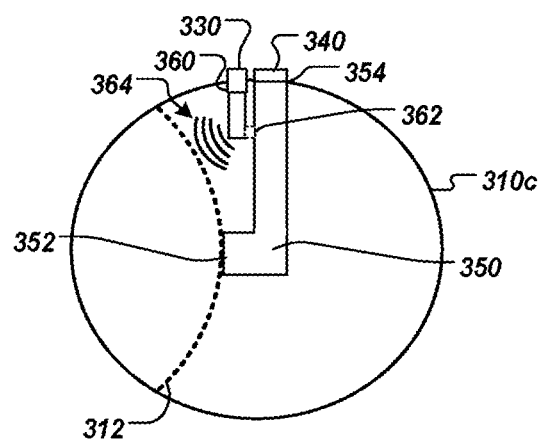
FIG. 3E is a drawing of a cross section of a mouthpiece having a channel connected to the pneumatic vibrator and the channel at an access port according to an example.

FIG. 3E is a drawing of a cross section of a mouthpiece 310c having a channel 360 connected to the pneumatic vibrator 330 and the channel 350 at an access port 362 according to an example. In an aspect, the pneumatic vibrator 330 is configured to create a cyclic negative pressure to enhance the tissue therapy by cycling the vacuum on and off to create a cyclic strain on the tissue. In an example, the cyclic negative pressure is configured to generate a vibration (364) at a therapeutic frequency. In an example, the cyclic negative pressure is a change between two or more negative pressures at a therapeutic frequency.

Figure 4A:
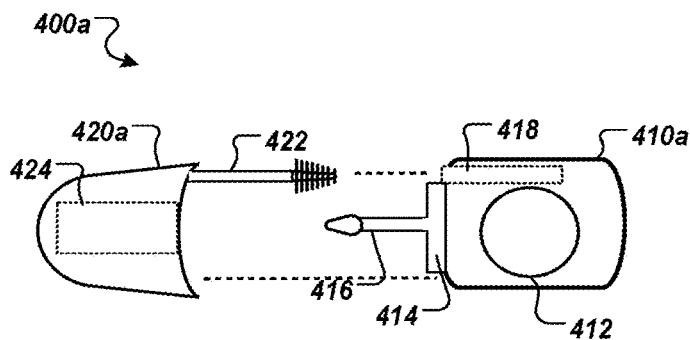
FIG. 4A is a drawing of an expanded view of a lip device including a mouthpiece having an applicator and a hollow tube, and an end cap having an exfoliating brush and a topical reservoir according to an example.
Figure 4B:
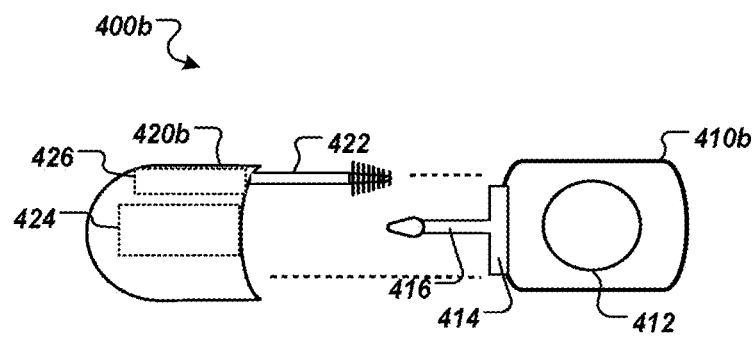
FIG. 4B is a drawing of an expanded view of a lip device including a mouthpiece having an applicator, and an end cap having a topical reservoir, an exfoliating brush, and a hollow tube configured to store the exfoliating brush according to an example.
Figure 4C:
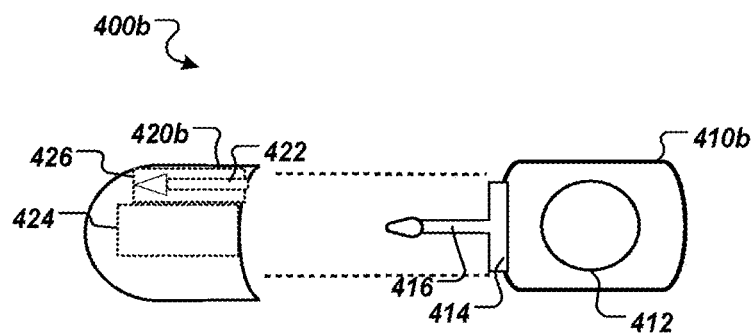
FIG. 4C is a drawing of an expanded view of the lip device shown in FIG. 4B where the exfoliating brush is stored within the hollow tube according to an example.

In an aspect, the therapeutic frequency is configured to prevent bruising of the lip tissue and to enhance the tissue therapy. In an example, the therapeutic frequency can be based on the mechanobiology properties of the lip tissue. Different frequencies target different layers of the tissue, such as targeting the mechanical receptors in the cell membranes of fibroblasts and keratinocytes within the lip tissue. This creates a signal cascade within the cells that cause them to create new extracellular matrix proteins. Examples of different frequency ranges in cosmetic devices which have beneficial effects on a user's skin are for example, a "low-frequency" range of about 30 hertz to about 50 hertz which primarily affects epidermis-associated proteins without substantially upregulating dermoepidermal-junction-associated proteins, and dermis-associated proteins; a "mid-frequency" range of about 50 hertz to about 100 hertz which affects all three layers of cutaneous proteins: epidermis-associated proteins, dermoepidermal-junction-associated proteins, and dermis-associated proteins; and a "high-frequency" range of about 100 hertz to about 140 hertz which affects epidermis-associated proteins and dermoepidermal-junction-associated proteins, but does not substantially affect dermis-associated proteins. The use of frequency ranges is described in each of U.S. PG. Pub. Nos. US2016/0184177A1, US2016/0184176A1, US2016/0184175A1, and US2016/0184171A1, which are incorporated herein by reference.
FIGS. 4A-4C In some implementations, the lip device can have a mouthpiece and an end cap with complementary features for storing the accessory attachments. FIG. 4A is a drawing of an expanded view of a lip device 400a including a mouthpiece 410a having an applicator plug 414 having a topical applicator 416 and a hollow tube 418 configured to house an exfoliating brush 422 connected to an end cap 420a according to an example. The end cap 420a can further have a topical reservoir 424 configured to receive the applicator plug 414 according to an example.

Figure 5A:
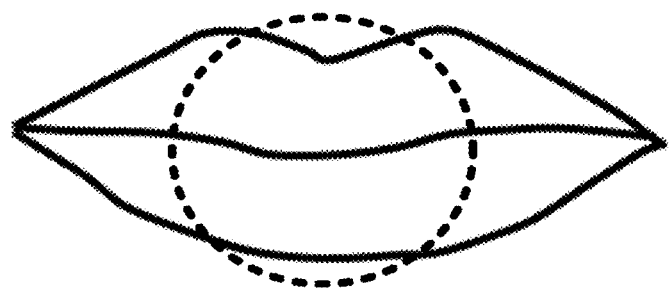
FIG. 5A is a drawing of a pair of lips and an outline of a mouthpiece according to an example.
Figure 5B:
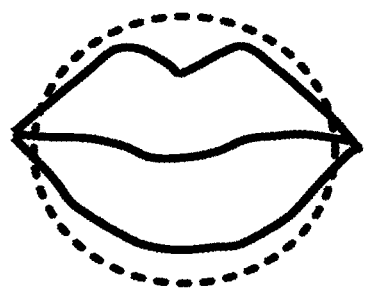
FIG. 5B is a drawing of a pair of puckered lips and an outline of a mouthpiece according to an example.
Figure 6A:
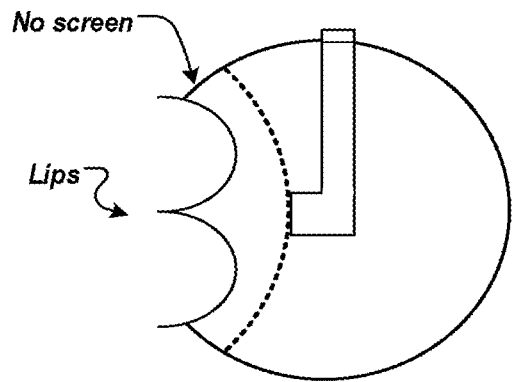
FIGS. 6A, 6B, and 6C illustrate the non-use and use of a screen element according to embodiments.
Figure 6B:
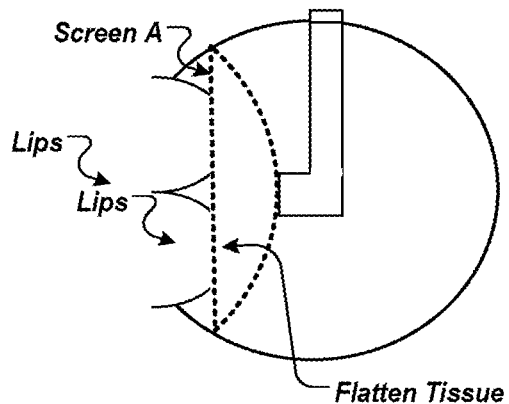

FIG. 4B is a drawing of an expanded view of a lip device 400b including a mouthpiece 410b having an applicator plug 414 having a topical applicator 416, and an end cap 420b having a topical reservoir 424, an exfoliating brush 422, and a hollow tube 426 configured to store the exfoliating brush 422 according to an example. FIG. 4C is a drawing of an expanded view of the lip device 400b where the exfoliating brush 422 is stored within the hollow tube 426 according to an example. In an example, the exfoliating brush 422 can be configured to either retract or flip back into the hollow tube 426.
FIGS. 5A-5B FIG. 5A shows of a pair of lips in a relaxed state and an outline of a mouthpiece according to an example. FIG. 5B is a drawing of a pair of "puckered" lips and an outline of a mouthpiece according to an example. The outline in each of these figures illustrates the contact point that the edge of the mouthpiece makes with the user's lip region depending on the state of the user's lips. It can be seen that the mouthpiece is configured to encompass substantially all of the user's lips when the user is in the puckered state.
FIGS. 6A-6B FIG. 6A shows a side view of the lips entering the chamber in the embodiments discussed above. FIG. 6B shows an alternative embodiment, in which there is a screen A disposed covering the entry of the chamber. The screen provides an advantage of modifying the spatial density of the stretching of the lips by flattening the tissue of the lips. Therefore, the device creates a desired amount of stretch across the lip even with a smaller pocket volume in the device. Thus, by isolating smaller sections of the lip with the screen, greater strain is created in each small element (i.e. stretching it further), without pulling the whole lip into the cavity with it.

Figure 6C:
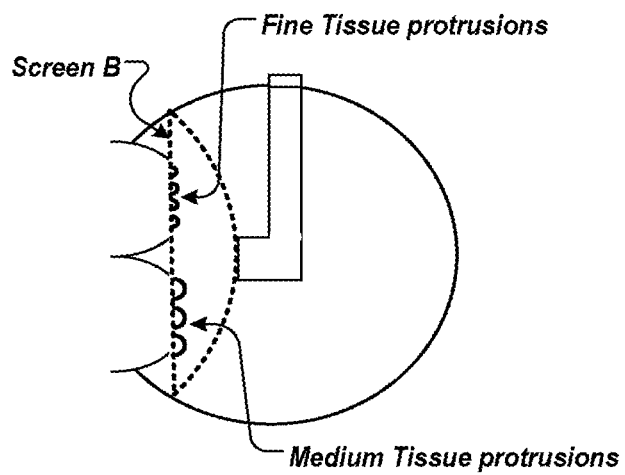

FIG. 6C shows an alternative embodiment in which there is a screen B which includes openings to allow protrusions of the lip tissue through the screen. The openings may be fine or medium sized, for example, for allowing fine tissue protrusions and/or medium tissue protrusions through the screen. Each of these examples above provide an advantage of modifying and varying the manner in which the user's lips are exposed to the negative pressure in the chamber.

Furthermore, the chamber volume does not need to be fixed, and it can be variable if necessary. Larger chamber volumes could allow for a greater strain to be imparted to the lip. Thus, a variable size chamber, either with the same device or over different devices, allows customization of the level of strain so that the appropriate tissue displacement is applied to different sized lips.

Additionally, there is an "ideal lip ratio" that is well known in the art of dermatology. The lower: upper lip ratio should be 1.6:1. Therefore, the present embodiments, and in particular the use of the above-described screen, allow for consumers to better achieve this ratio by focusing on improving the volume in the lip in select areas that they need. Also, the contour 114 (cupping curvature) of the device can be specially designed to help consumers better achieve the ideal lip volume ratio discussed above.

A benefit of the device according to the above-described embodiments is that it will be smaller, more compact, travel friendly and quieter than other devices in the conventional art. Thus, the present design and functional modifications of the present embodiments are more desirable to the consumer since a device meeting all of these criteria does not exist on the market today.

The present embodiments allow consumers to achieve (i) immediate benefits in lip volume/plumping and natural lip color enhancement and (ii) longer term lip volume/plumping benefits after daily use (vs. initial baseline). The present embodiments further provide an advantage of delivering multiple lip enhancement benefits without the need for injections, needles, potential side effects, surgery or potentially skin sensitizing chemicals that are commonly used to achieve lip enhancement effects.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernable variants of the teachings herein, define, in part, the scope of the foregoing claim terminology such that no inventive subject matter is dedicated to the public.

What is claimed is:

1. An apparatus for lip conditioning, comprising:
   a mouthpiece having an opening, a cupping contour of the opening being configured to press against a portion of tissue or lips of a user;
   a chamber configured to receive the portion of the tissue or lips of the user through the opening; and
   a screen disposed covering the opening, wherein the screen includes openings configured to allow protrusions of the lip tissue through one or more portions of the screen, the screen including a first size of openings to allow a first size of protrusions of the lip tissue only at an upper portion of the screen and a second size of openings to allow a second size of protrusions of the lip tissue only at a lower portion of the screen, the second size being larger than the first size,
   wherein the apparatus is configured to generate suction within the chamber, and to apply a negative pressure to the portion of tissue or lips of the user.

2. The apparatus according to claim 1, wherein the negative pressure is configured to allow the blood vessels within the tissue or lips of the user to fill with blood and to trigger an inflammatory response of chemicals.

3. The apparatus according to claim 1, wherein the cupping contour of the opening of the mouthpiece has a contoured edge configured to press against the portion of tissue or lips of the user.

4. The apparatus according to claim 1, further comprising an access port disposed at a surface inside the chamber which connects to a pressure valve.

5. The apparatus according to claim 4, wherein the access port includes a sensor that connects to an indicator on an exterior surface of the apparatus for indicating that a pressure change has occurred in the chamber.

6. The apparatus according to claim 1, further comprising at least one compartment configured to hold one or more accessories.

7. The apparatus according to claim 6, wherein the one or more accessories include at least one of a topical applicator, a lipstick tube, and an exfoliator.

8. The apparatus according to claim 7, wherein the at least one compartment includes at least two compartments disposed on opposite sides of the chamber, and at least two of the topical applicator, lipstick tube, and exfoliator are separately disposed in the at least two compartments respectively.

9. The apparatus according to claim 6, wherein the at least one compartment includes a removable cap, an inner surface of which forms a portion of the at least one compartment.

10. The apparatus according to claim 9, wherein the at least one compartment is configured to hold at least two of the one or more accessories, where one of the at least two accessories is configured to attach to a surface of the removable cap.

11. The apparatus according to claim 6, wherein the at least one compartment includes an applicator interface configured to connect with any one of the one or more accessories such that the one or more accessories are interchangeable.

12. The apparatus according to claim 1, further comprising a gauge indicator connected to the chamber that includes a spring and a piston which is configured to move based on a change in an amount of suction pressure in the chamber.

13. The apparatus according to claim 1, further comprising a pneumatic vibrator configured to generate a vibration at a predetermined frequency.

14. The apparatus according to claim 13, wherein the pneumatic vibrator is configured to generate a cyclic negative pressure at the predetermined frequency.

15. The apparatus according to claim 1, wherein the apparatus is configured to apply a cyclic negative pressure to the portion of tissue or lips.

16. The apparatus according to claim 1, wherein the apparatus is configured to apply a cyclic negative pressure to the portion of tissue or lips of a frequency and for a duration sufficient to elicit blood within the tissue or lips.

17. The apparatus according to claim 1, wherein the apparatus is configured to apply a cyclic negative pressure to the portion of tissue or lips of a frequency to elicit blood within the tissue or lips.

18. The apparatus according to claim 1, wherein the apparatus is configured to apply a cyclic negative pressure to the portion of tissue or lips of an amplitude and for a duration sufficient to elicit blood within the tissue or lips.

* * * * *